United States Patent
Buck et al.

(10) Patent No.: US 9,550,019 B2
(45) Date of Patent: Jan. 24, 2017

(54) CAPILLARY DIALYZERS

(71) Applicant: GAMBRO LUNDIA AB, Lund (SE)

(72) Inventors: Reinhold Buck, Alleshausen (DE);
Roland Henle, Haigerloch-Stetten (DE); Juergen Eichinger, Bisingen (DE)

(73) Assignee: Gambro Lundia AB, Lund (SE)

( * ) Notice: Subject to any disclaimer, the term of this patent is extended or adjusted under 35 U.S.C. 154(b) by 44 days.

(21) Appl. No.: 14/409,201

(22) PCT Filed: Jun. 20, 2013

(86) PCT No.: PCT/EP2013/062821
§ 371 (c)(1),
(2) Date: Dec. 18, 2014

(87) PCT Pub. No.: WO2013/190022
PCT Pub. Date: Dec. 27, 2013

(65) Prior Publication Data
US 2015/0165106 A1    Jun. 18, 2015

(30) Foreign Application Priority Data
Jun. 21, 2012   (EP) .................................... 12172902

(51) Int. Cl.
*A61M 1/16*       (2006.01)
*B01D 61/28*      (2006.01)
(Continued)

(52) U.S. Cl.
CPC ........... *A61M 1/1623* (2014.02); *A61M 1/165* (2014.02); *B01D 61/243* (2013.01); *B01D 61/28* (2013.01);
(Continued)

(58) Field of Classification Search
CPC ................ A61M 1/1623; A61M 1/165; A61M 2202/0413; A61M 2205/75; A61M 2207/00; B01D 2313/04; B01D 2313/21; B01D 61/243; B01D 63/02; B01D 63/021; B01D 65/003; B01D 61/28
See application file for complete search history.

(56) References Cited

U.S. PATENT DOCUMENTS

| 6,074,559 A | 6/2000 | Hahmann et al. |
| 2003/0029785 A1 | 2/2003 | Dannenmaier |
| 2010/0170850 A1 | 7/2010 | Heilmann et al. |

FOREIGN PATENT DOCUMENTS

| DE | 19744336 | 10/1997 |
| EP | 0305687 | 7/1988 |

(Continued)

OTHER PUBLICATIONS

PCT Search Report and Written Opinion for PCT/EP2013/062821, completed Aug. 12, 2013.

*Primary Examiner* — John Kim
(74) *Attorney, Agent, or Firm* — Banes & Thornburg LLP

(57) ABSTRACT

A capillary dialyzer comprises: a) a housing; a bundle of semi-permeable hollow fiber membranes; c) end walls supporting the first and second ends of the hollow fiber membranes; d) a first end cap covering a first end of the housing and a second end cap covering a second end of the housing; e) an inlet and an outlet; f) support rings; and g) sealing rings interposed between the end wall and the first end cap and between the end wall and the second end cap, respectively. A circular groove of the end cap which receives the wall of the housing comprises indentations for creating a fluid connection between the inside of the capillary dialyzer and its exterior when the end caps are mounted on the housing but have not yet been welded to the housing.

20 Claims, 13 Drawing Sheets

(51) Int. Cl.
*B01D 63/02* (2006.01)
*B01D 65/00* (2006.01)
*B01D 61/24* (2006.01)

(52) U.S. Cl.
CPC ............ *B01D 63/02* (2013.01); *B01D 63/021* (2013.01); *B01D 65/003* (2013.01); *A61M 2202/0413* (2013.01); *A61M 2205/75* (2013.01); *A61M 2207/00* (2013.01); *B01D 2313/04* (2013.01); *B01D 2313/21* (2013.01)

(56) References Cited

FOREIGN PATENT DOCUMENTS

| EP | 0844015 | 5/1998 |
|----|---------|--------|
| EP | 1323462 | 7/2003 |
| EP | 2156881 | 2/2010 |
| JP | H08229359 | 9/1996 |
| WO | WO92/12787 | 8/1992 |
| WO | WO01/60477 | 8/2001 |
| WO | WO01/60502 | 8/2001 |
| WO | WO2010/051912 | 5/2010 |

CAPILLARY DIALYZERS

CROSS REFERENCE TO RELATED APPLICATIONS

This application is the U. S. national phase of PCT/EP2013/062821 filed Jun. 20, 2013. PCT/EP2013/062821 claims priority under the Convention to European patent application 12172902.4, filed Jun. 21, 2012. EP12172902.4 and PCT/EP2013/062821 are hereby incorporated herein in their entireties by this reference.

TECHNICAL FIELD

The present invention relates to capillary dialyzers for blood purification.

BACKGROUND OF THE INVENTION

Capillary dialyzers are widely used for blood purification in patients suffering from renal insufficiency, i.e., for treatment of the patients by hemodialysis, hemodiafiltration or hemofiltration. A multitude of different models of capillary dialyzers is commercially available.

The devices generally consist of a casing comprising a tubular section with end caps capping the mouths of the tubular section. A bundle of hollow fiber membranes is arranged in the casing in a way that a seal is provided between the first flow space formed by the fiber cavities and a second flow space surrounding the membranes on the outside. Examples of such devices are disclosed in EP 0 844 015 A2, EP 0 305 687 A1, and WO 01/60477 A2.

There is a continuing desire to further improve such capillary dialyzers, e.g., in terms of performance, efficiency, reliability, safety, handling, and other properties.

SUMMARY OF THE INVENTION

It is an object of the present invention to provide capillary dialyzers with improved properties.

The capillary dialyzers of the present invention comprise housings and end caps of optimized construction.

The capillary dialyzers of the present invention comprise particular hollow fiber membranes exhibiting optimized performance.

SHORT DESCRIPTION OF THE DRAWINGS

DETAILED DESCRIPTION

Figure 1:
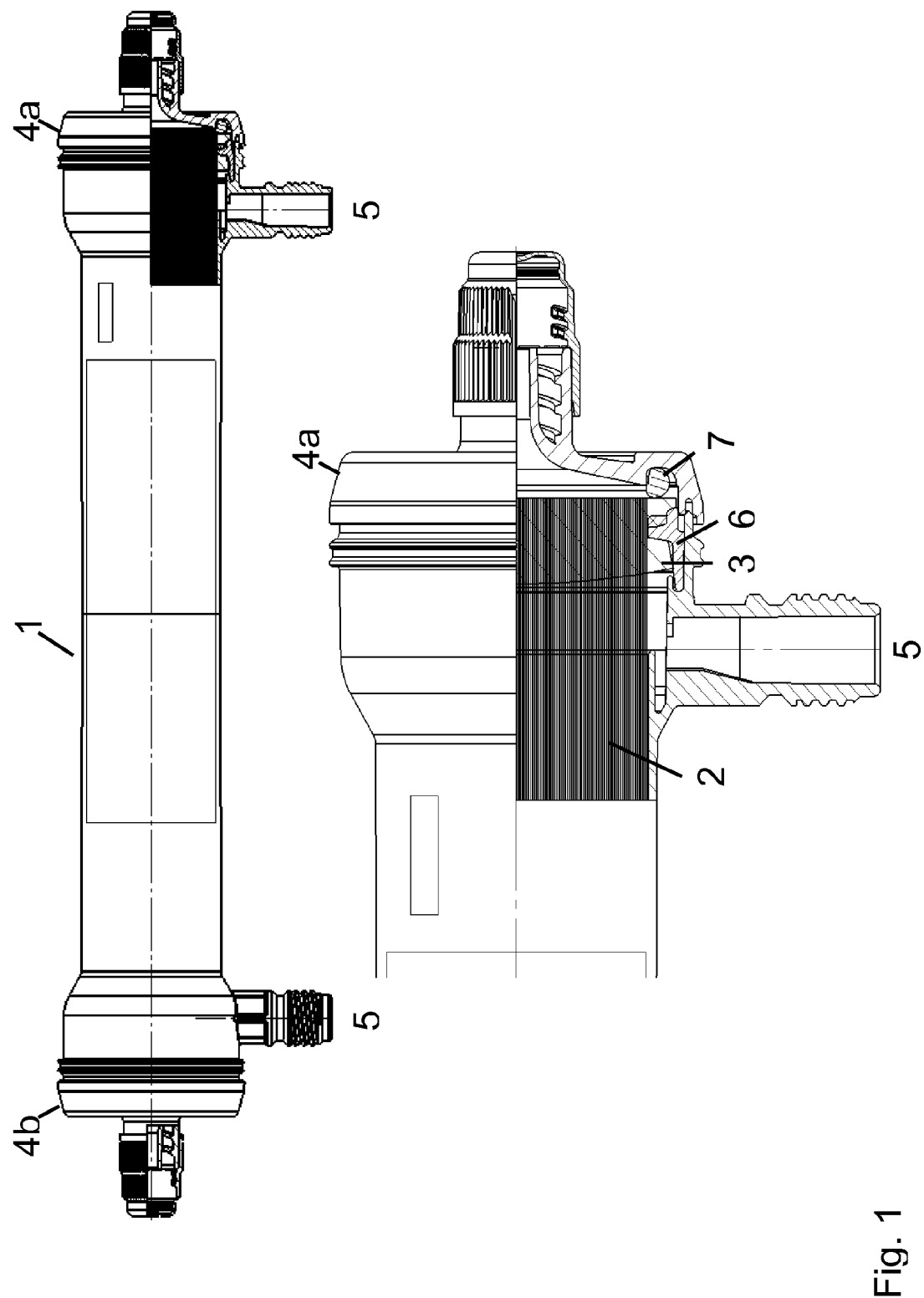
FIG. 1 shows a side, partially cross-sectional view of a capillary dialyzer.

FIG. 1 shows a capillary dialyzer comprising:
a) a housing (1) defining a longitudinally extending internal chamber including a first end and a second end;
b) a bundle of semi-permeable hollow fiber membranes (2) disposed within the internal chamber and extending longitudinally from the first end of the housing to the second end of the housing, the hollow fiber membranes having an outer surface, and a first end and a second end corresponding to the first end and the second end of the internal chamber;
c) end wall means (3) supporting the first and second ends of the hollow fiber membranes within the internal chamber so as to sealingly separate the first and second ends of the hollow fiber membranes from the outer surface of the hollow fiber membranes between the first and second ends thereof;
d) a first end cap (4a) covering the first end of the housing and a second end cap (4b) covering the second end of the housing, the first and second end caps being applied to the first and second ends of the housing in a fluid-tight manner;
e) an inlet (5) for the introduction of a fluid into the internal chamber and an outlet (5) for the evacuation of a fluid from the internal chamber at a location between the first and second end of the housing;
f) support rings (6) disposed between the end wall means and the housing at the first and second ends of the internal chamber; and
g) sealing rings (7) interposed between the end wall and the first end cap (4a) and between the end wall and the second end cap (4b), respectively.

The diameter of the housing (1) of the capillary dialyzers of the present invention is not uniform. The housing (1) has a middle section where the inner diameter is smaller than at the ends of the housing (1). In one embodiment of the invention, the inner diameter of the middle section of the housing (1) is 31.5±0.1 mm; and the inner diameter of the mouth of the housing (1) is 45.9±0.1 mm. In another embodiment of the invention, the inner diameter of the middle section of the housing (1) is 34.0±0.1 mm; and the inner diameter of the mouth of the housing (1) is 45.9±0.1 mm. In still another embodiment of the invention, the inner diameter of the middle section of the housing (1) is 38.0±0.1 mm; and the inner diameter of the mouth of the housing (1) is 49.6±0.1 mm.

The overall length of the housing (1) of the capillary dialyzers of the present invention is 255.8±0.3 mm; the distance between the centers of the inlet (5) and outlet (5) is 218.6±0.3 mm.

Figure 4:
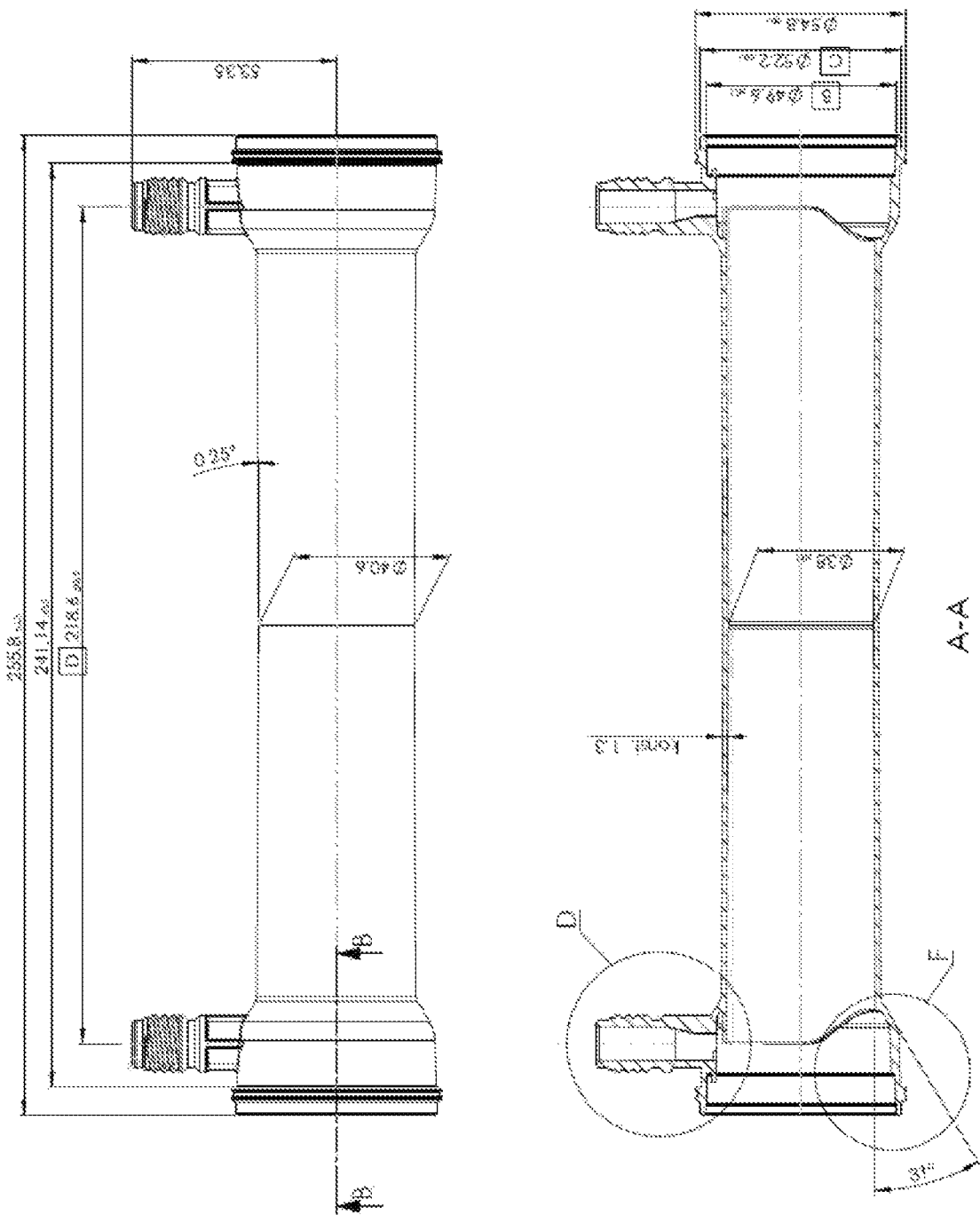
FIG. 4 shows a side view and a cross-sectional side view of an embodiment of the housing of the capillary dialyzers of the present invention.
Figure 4A:
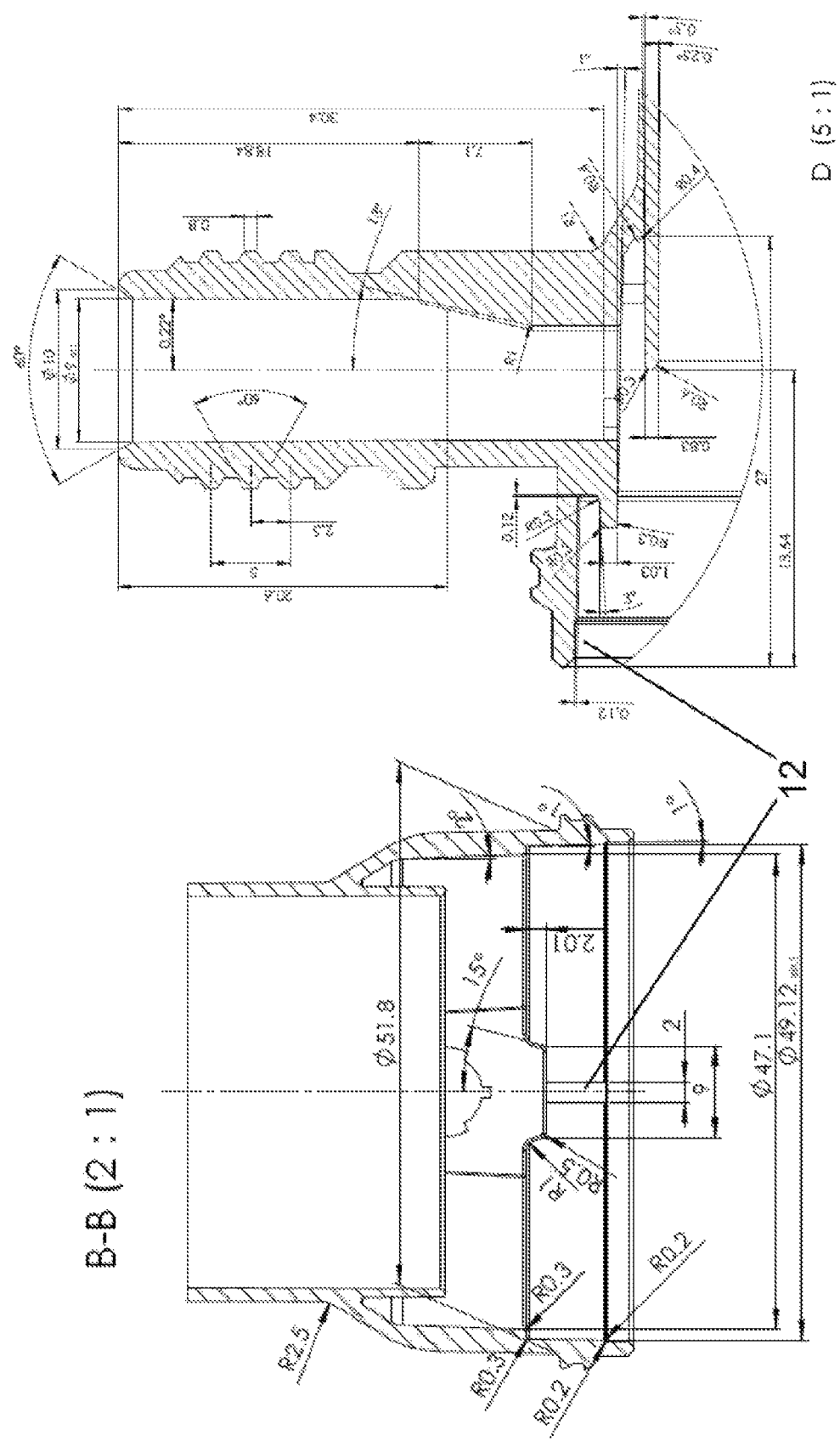
FIG. 4a shows detailed views of cross-section B-B and section D of the embodiment shown in FIG. 4.
Figure 4B:
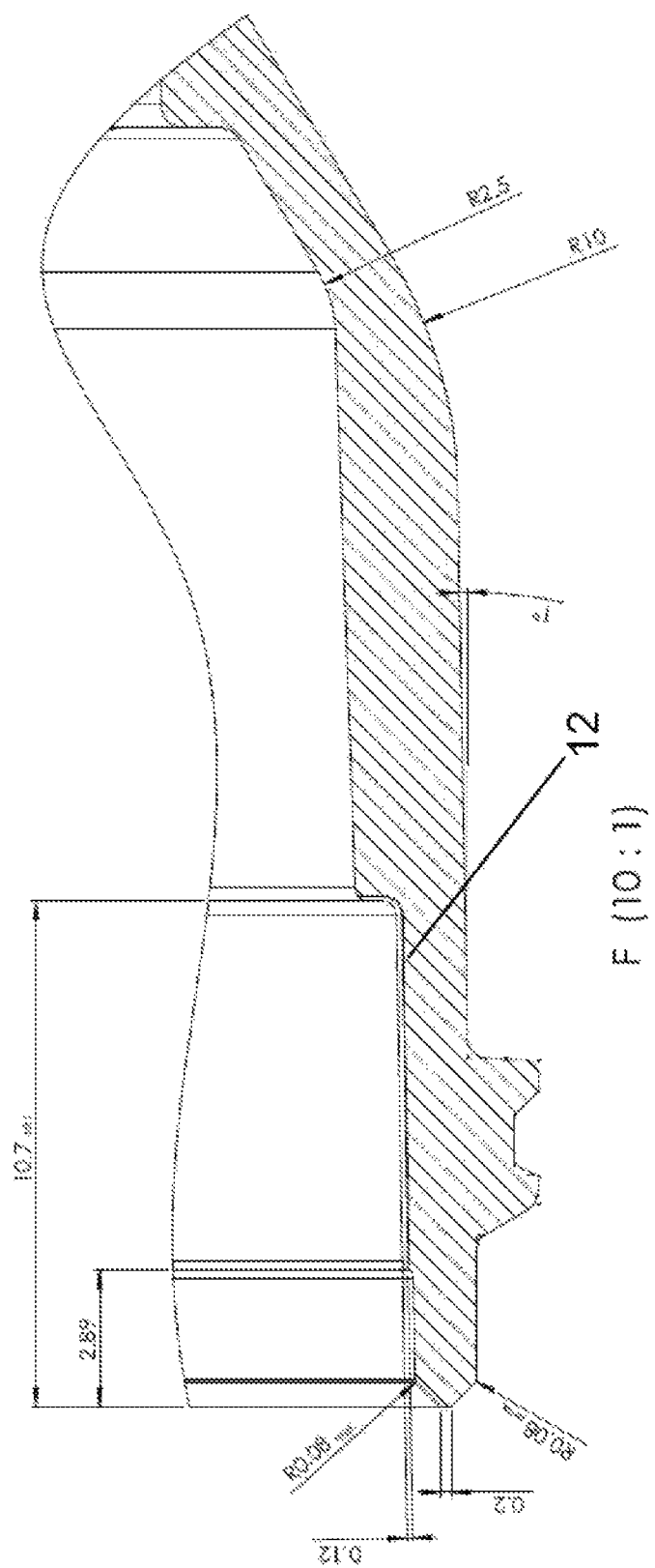
FIG. 4b shows a detailed view of section F of the embodiment shown in FIG. 4.
Figure 5:
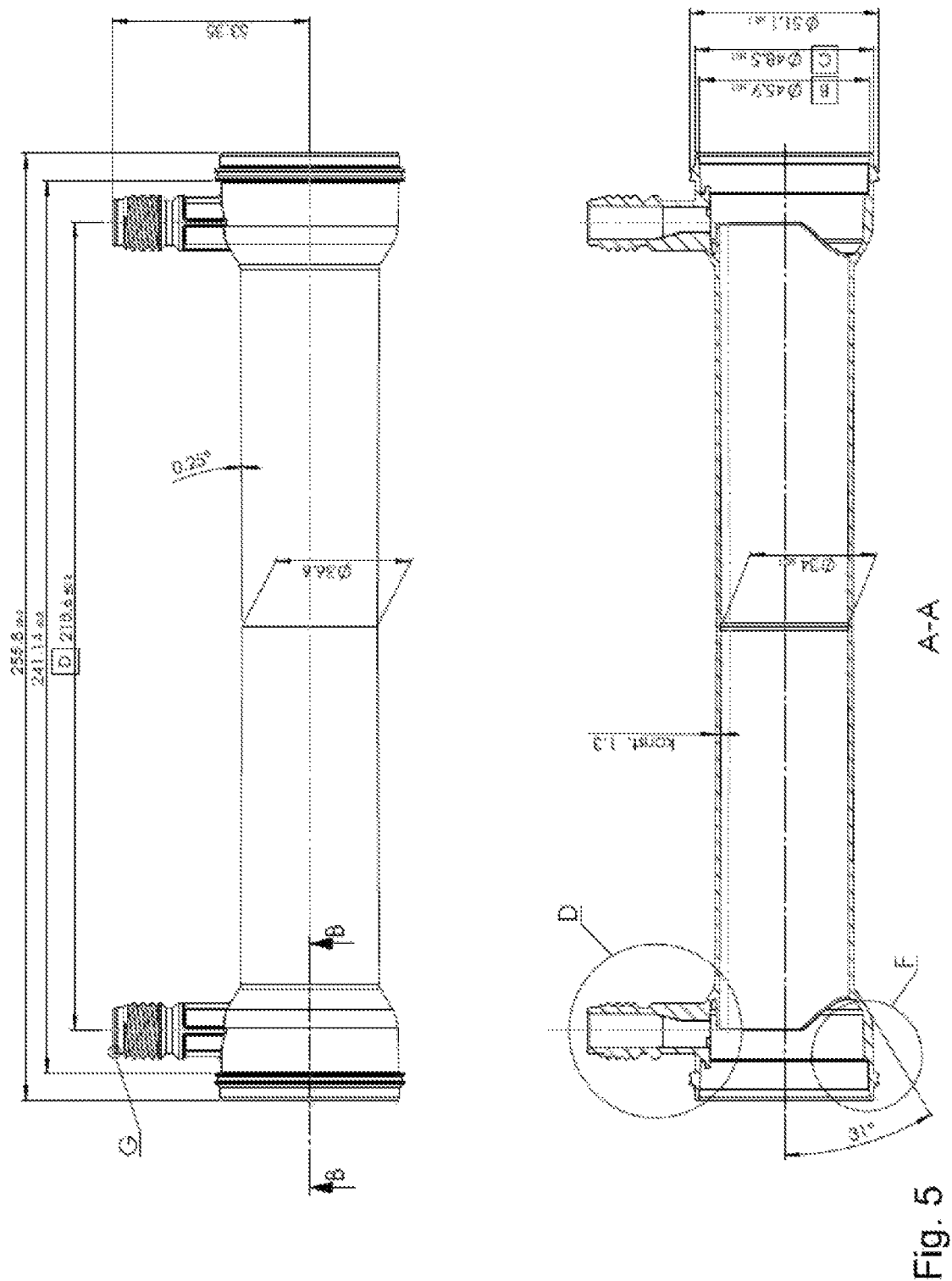
FIG. 5 shows a side view and a cross-sectional side view of another embodiment of the housing of the capillary dialyzers of the present invention.
Figure 5A:
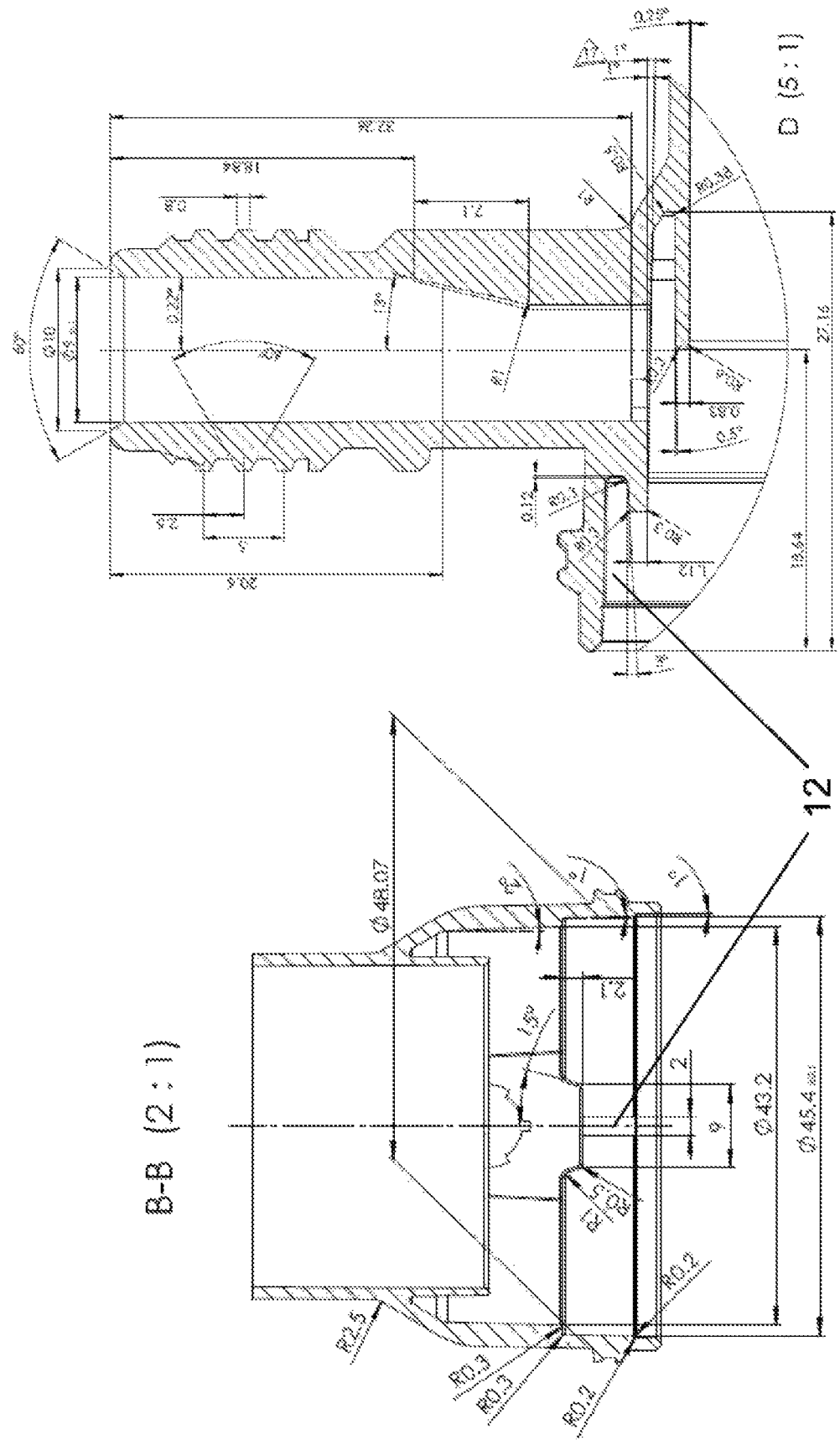
FIG. 5a shows detailed views of cross-section B-B and section D of the embodiment shown in FIG. 5.
Figure 5B:
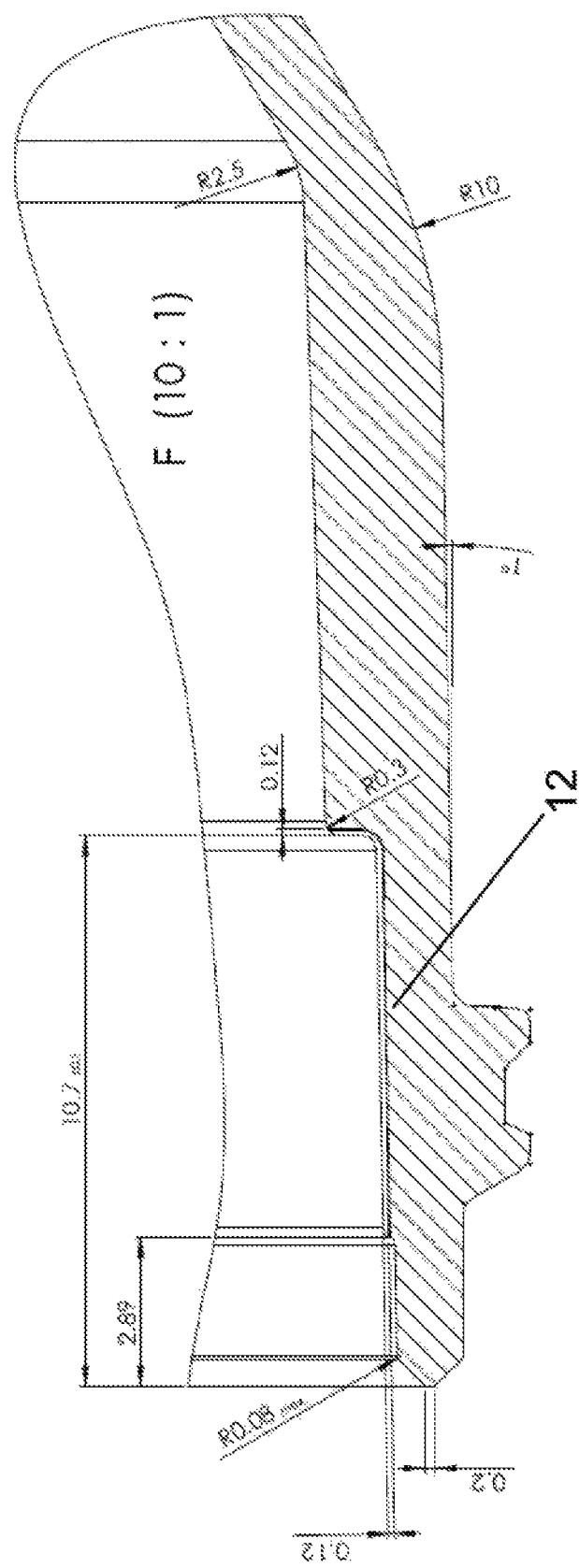
FIG. 5b shows a detailed view of section F of the embodiment shown in FIG. 5.
Figure 6:
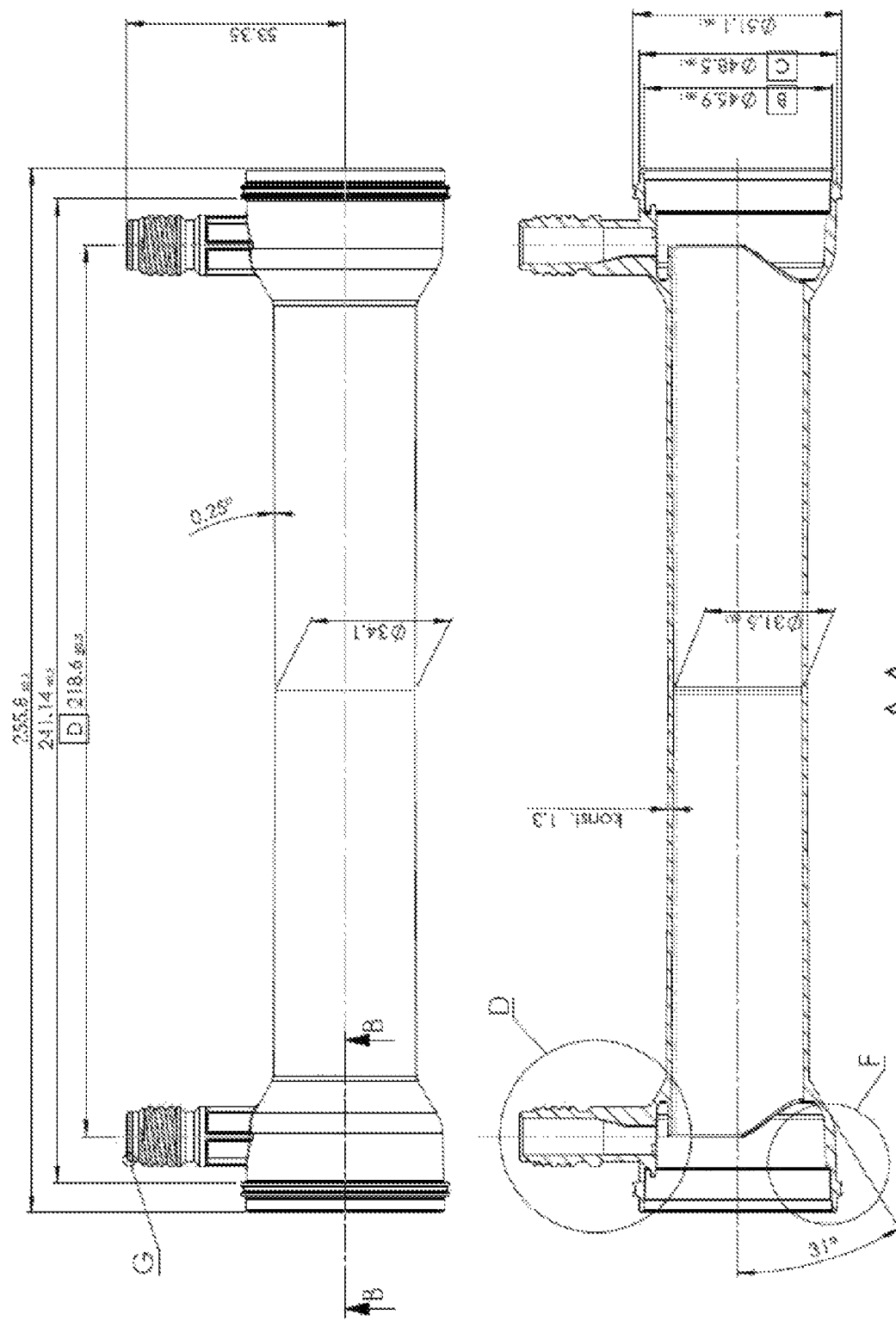
FIG. 6 shows different views of still another embodiment of the housing of the capillary dialyzers of the present invention.
Figure 6A:
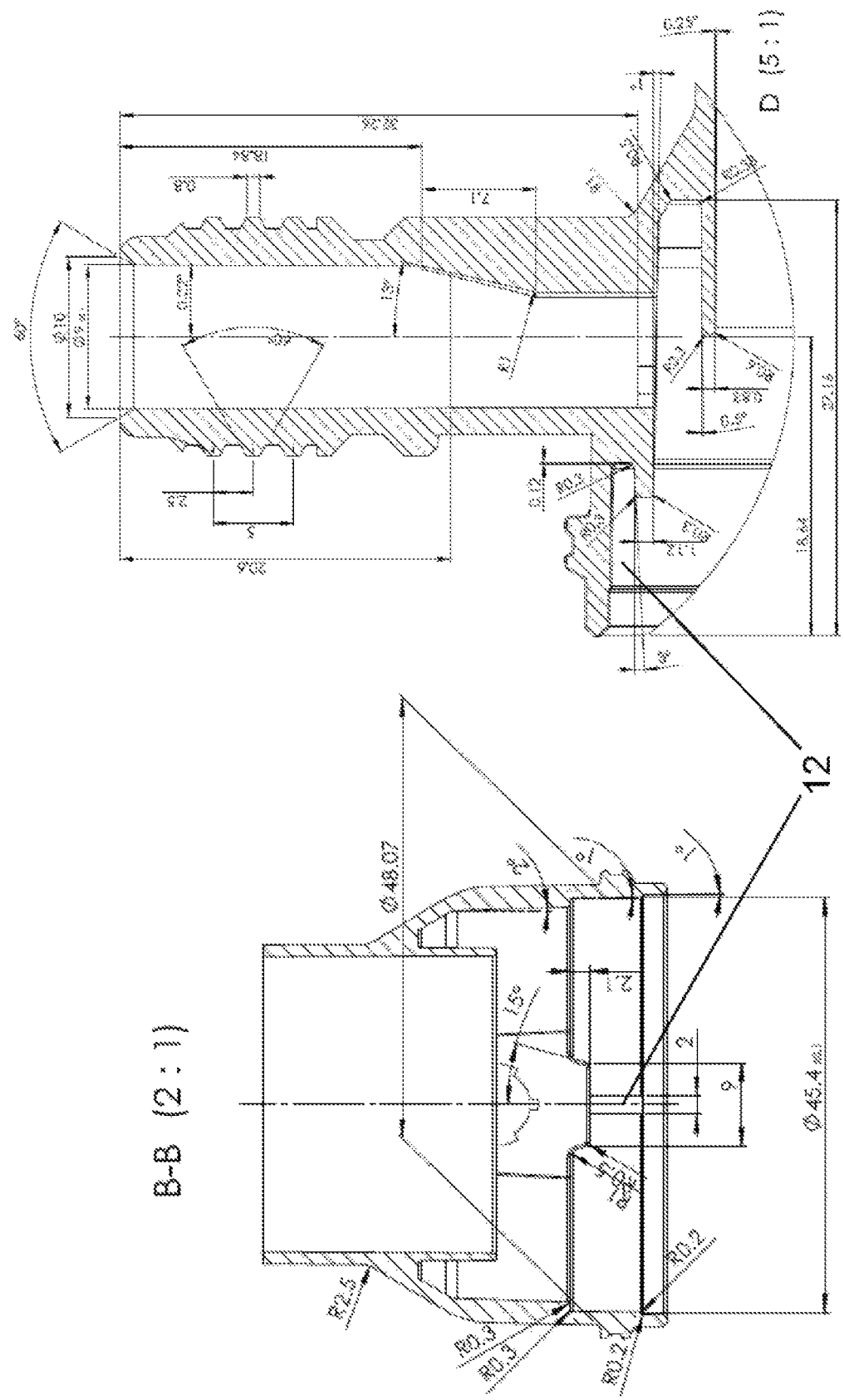
FIG. 6a shows detailed views of cross-section B-B and section D of the embodiment shown in FIG. 6.
Figure 6B:
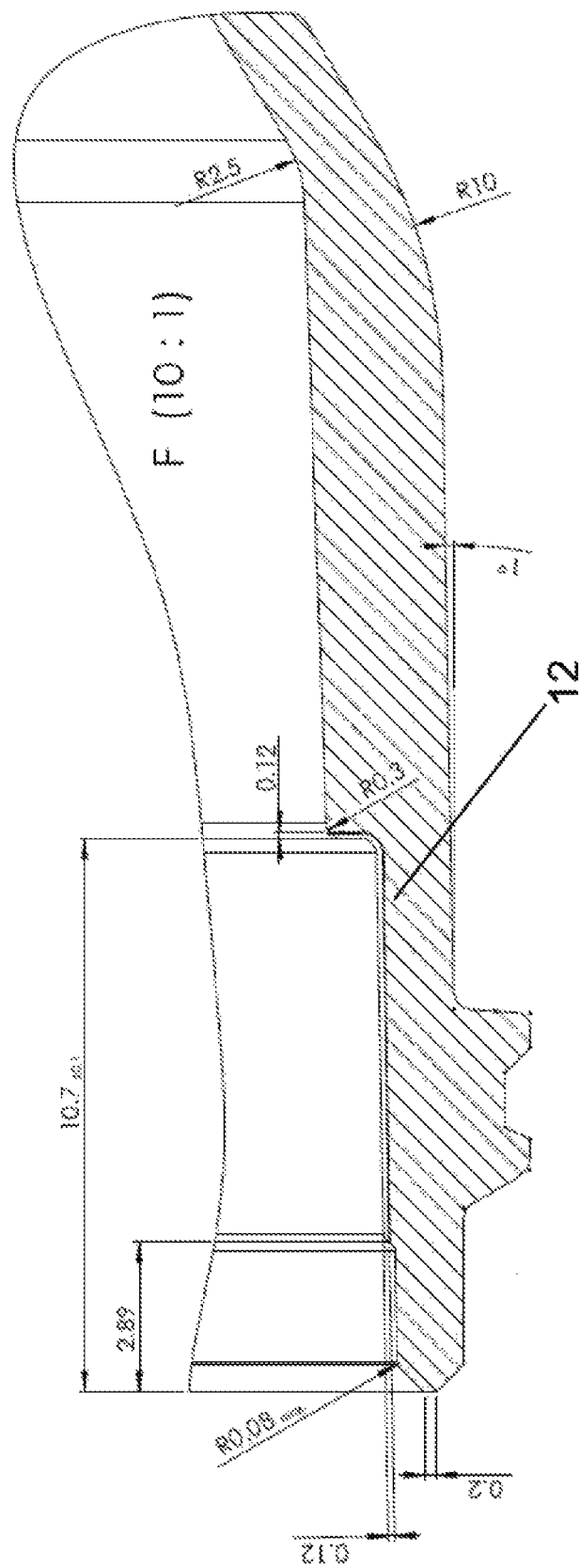
FIG. 6b shows a detailed view of section F of the embodiment shown in FIG. 6.

The header sections of the housing (1) comprise notches (12) on the inside surface which assist in creating a fluid connection between the inside of the device and its exterior when the end caps (4a, 4b) are mounted on the housing (1) but have not yet been welded to the housing (1). In the embodiments shown in FIGS. 4 to 6 (particularly detailed views D and F and cross section B-B, respectively), two such notches (12) are provided in each header section. In these embodiments, the notches (12) are 2 mm wide and 0.12 mm deep and are located opposite to each other, extending from the mouth of the housing (1) to the end of a ledge inside the housing (1) on which the support ring (6) is positioned, thus enabling air to pass the outside of the support ring (6). The notches (12) act together with the indentations (8) in the end caps (4a, 4b) which will be described in detail below.

The housing (1) and the end caps (4a, 4b) of the capillary dialyzers of the present invention are usually made of a transparent polymer, e.g. polyethylene, polypropylene, polyesters like PET or PBT, polymethylmethacrylate, polystyrene (HIPS) or polycarbonate. The potting material for the hollow fiber membranes usually is polyurethane.

In one embodiment of the device of the invention, the housing (1) and end caps (4a, 4b) are made of polycarbonate, the potting material forming the end wall means (3) is made of polyurethane, the support rings (6) are made of polypropylene and the sealing rings (7) are made of silicone rubber.

Figure 2A:
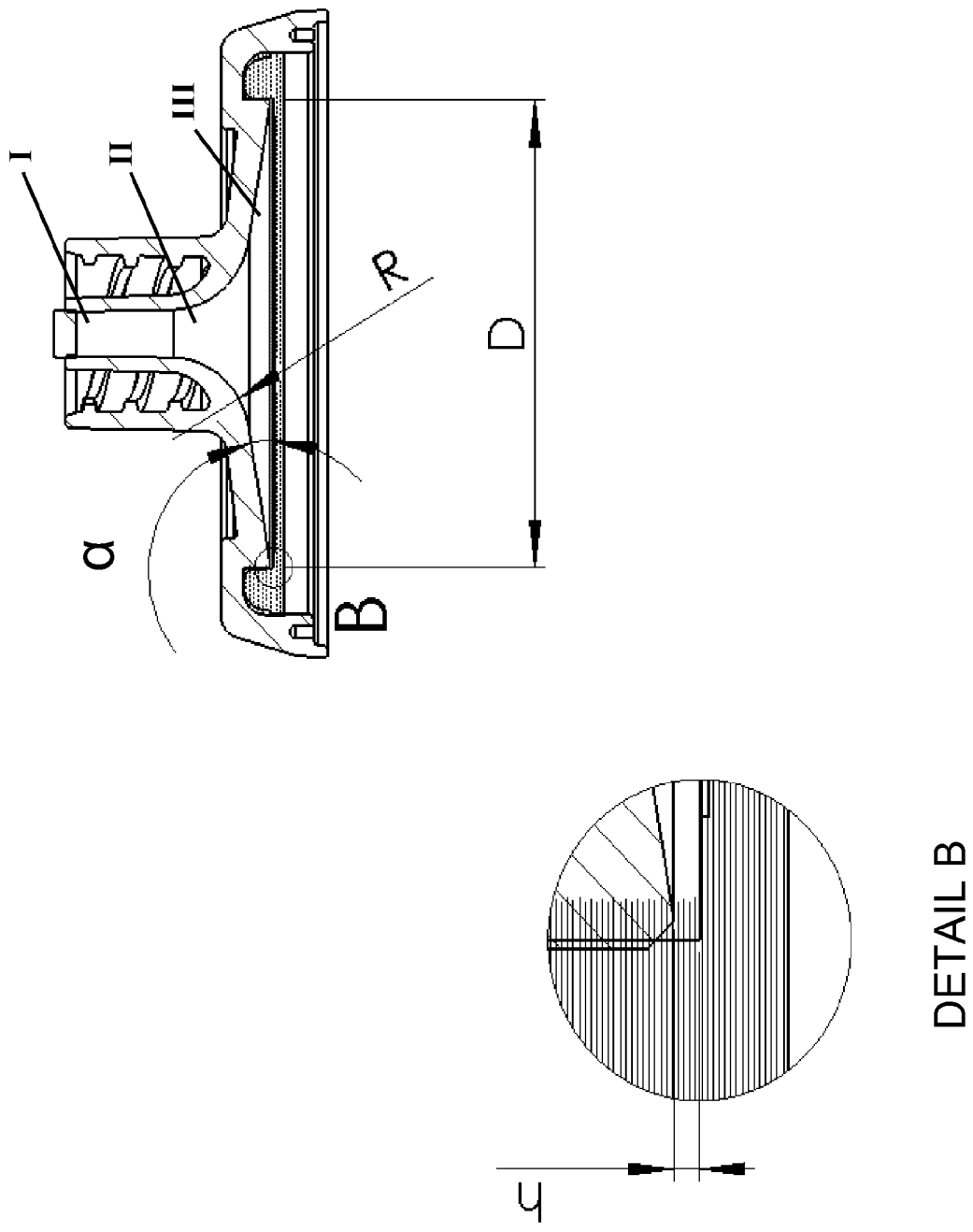
FIG. 2a shows a schematic cross-sectional side view of an embodiment of the end cap of the capillary dialyzers of the present invention. The shaded area represents a portion of a filtration device sealed by the end cap.
Figure 2B:
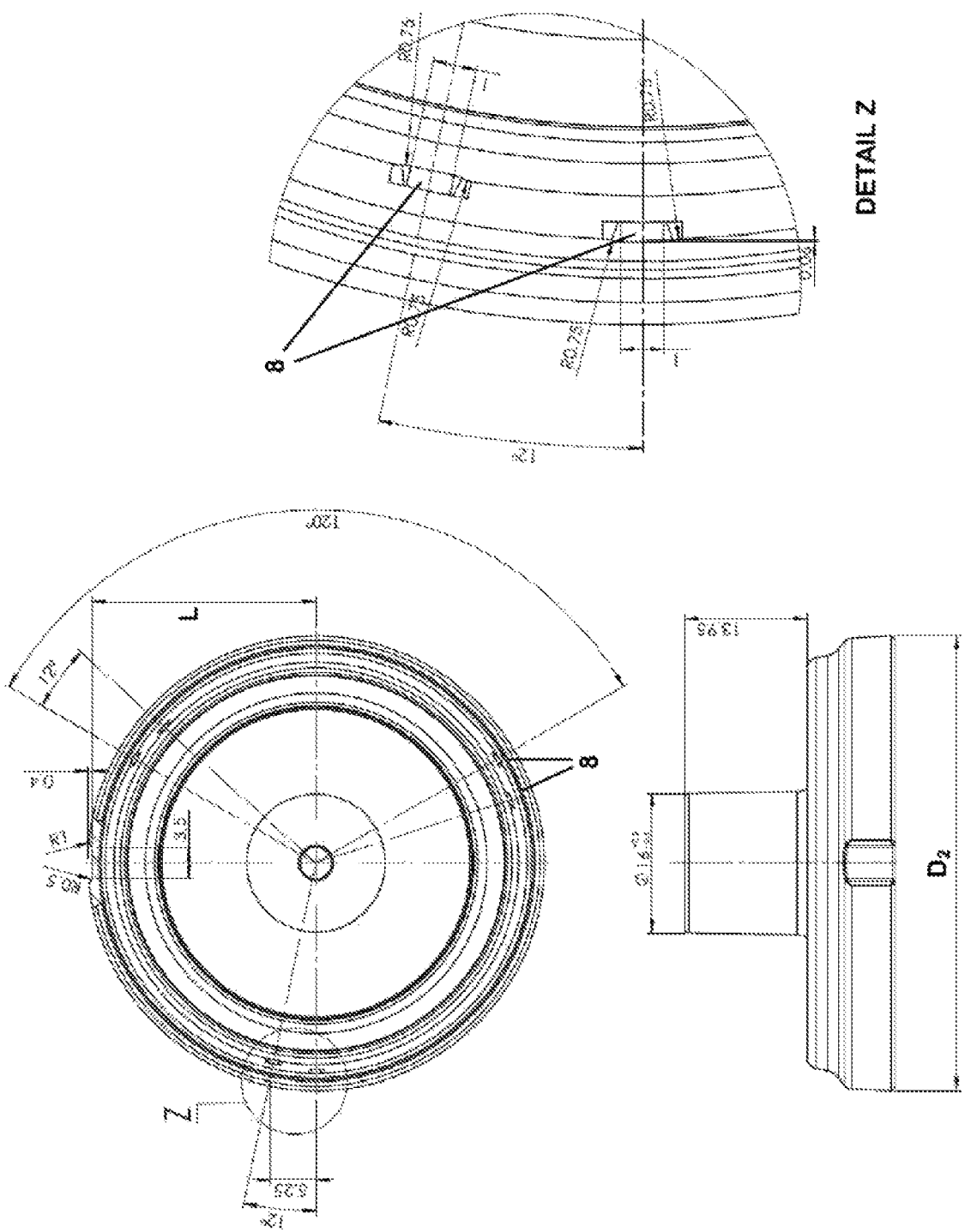
FIG. 2b shows a bottom view and a side view of an embodiment of the end cap of the capillary dialyzers of the present invention.

FIGS. 2a and 2b show an embodiment of the end cap (4a, 4b) of the capillary dialyzers of the present invention. As shown in FIGS. 2a and 2b, the end cap (4a, 4b) comprises an inlet or outlet, respectively, for a liquid, arranged axially in the center of the end cap (4a, 4b). A two-start thread which fits a standard blood-line connector is provided round the inlet or outlet, as the case may be. Starting from the mouth of the end cap (4a, 4b), the inner diameter of the inlet or outlet, as the case may be, is constant or increases linearly in a first section (I) of the end cap, then widens gradually, with a constant curvature R, in a second section (II) until the inner surface includes a predetermined angle α with the horizontal. The diameter then increases linearly in a third section (III), until a predetermined diameter D is reached. At diameter D, the fluid compartment formed by the inside of the end caps (4a, 4b) and the lumen of the hollow fiber membranes, when the end caps (4a, 4b) are placed on the mouths of the tubular housing of the device, is sealed off by a sealing ring (7) placed in a circular groove provided in the end caps (4a, 4b). When the device is assembled, the minimum distance between the inner surface of the end cap (4a, 4b) and the plane defined by the ends of the hollow fiber membranes is h.

The inner surface of the end cap (4a, 4b) is axially symmetrical with regard to the longitudinal axis of the inlet/outlet, which is also the longitudinal axis of the end cap (4a, 4b). The inner surface has the form of a funnel comprising, in the direction of increasing diameter, a first section (I) taking the form of a cylinder or a truncated cone, a middle section (II) taking the form of a torus segment, and a third section (III) taking the form of a truncated cone.

In one embodiment of the invention, the diameter D is 36.1±0.1 mm. In another embodiment of the invention, the diameter D is 39.8±0.1 mm.

In one embodiment of the invention, the radius R of the middle section (II), i.e., the curvature R is in the range of from 6 to 8 mm, e.g., 7 mm.

In one embodiment of the invention, the distance h has a value in the range of from 1.5 mm to 2.0 mm.

In one embodiment of the invention, the aperture of the first section (I) from the inlet to the middle section is in the range of from 0° to 4°, e.g. from 1° to 3°, in particular from 1.5° to 2.5°.

In a particular embodiment of the end cap (4a, 4b) for the capillary dialyzers of the invention, the top of the first section (I), i.e., the inlet of the end cap (4a, 4b), has a diameter of 3.7±0.1 mm, the aperture of the first section (I) from the inlet to the middle section is 2.0±0.1°, and R is 7.0±0.1 mm.

In one embodiment of the end cap (4a, 4b) for the capillary dialyzers of the invention, α is 8.85±0.05°. In another embodiment of the end cap (4a, 4b) of the invention, α is 9.53±0.05°.

In one embodiment of the invention, the outer diameter $D_2$ of the end cap (4a, 4b) is 52.1±0.1 mm. In another embodiment of the invention, the outer diameter $D_2$ is 55.8±0.1 mm.

In one embodiment of the invention, the distance L is 25.65±0.1 mm. In another embodiment of the invention, the distance L is 27.45±0.1 mm.

In one embodiment of the end cap (4a, 4b) for the capillary dialyzers of the invention, α is 8.85±0.05°, the diameter D is 36.1±0.1 mm, R is 7.0±0.1 mm, and the outer diameter $D_2$ of the end cap (4a, 4b) is 52.1±0.1 mm.

In another embodiment of the end cap (4a, 4b) for the capillary dialyzers of the invention, α is 9.53±0.05°, the diameter D is 39.8±0.1 mm, R is 7.0±0.1 mm, and the outer diameter $D_2$ of the end cap (4a, 4b) is 55.8±0.1 mm.

As shown in FIG. 2b top left and detailed view Z, indentations (8) are provided in the circular groove of the end cap (4a, 4b) which receives the wall of the housing (1). These indentations create a fluid connection between the inside of the device and its exterior when the end caps (4a, 4b) are mounted on the housing (1) but have not yet been welded to the housing. This is an additional safety feature which makes sure that only filters having both end caps (4a, 4b) properly welded to the housing (1) can pass the final integrity test of the capillary dialyzers.

In one embodiment of the end cap (4a, 4b) for the capillary dialyzers of the invention shown in FIG. 2b, three pairs of indentations are provided. In this particular embodiment, the two indentations of each pair are displaced by 12°, and the angle between the pairs is 120°.

Figure 3:
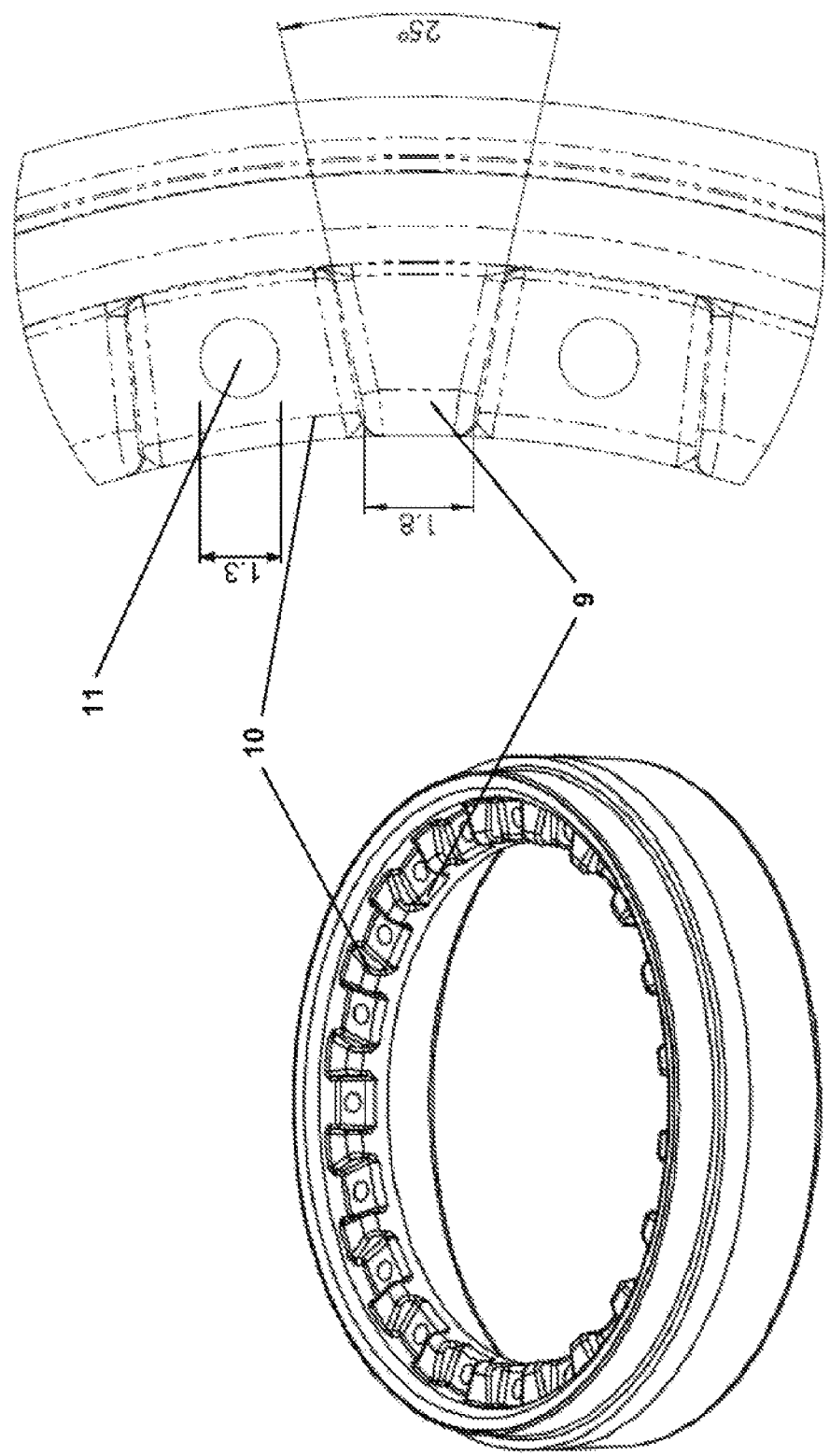
FIG. 3 shows a schematic perspective view and a detail of a top view of an embodiment of the support ring of the capillary dialyzers of the present invention.

The support ring (6) for the capillary dialyzers of the invention is shown in FIG. 3. The support ring features 20 ridges (9) evenly distributed over its circumference. The ridges are separated by level sections (10) containing through bores (11). Thus, the ridges are displaced from each other by 18°. Likewise, the through bores (11) also are displaced from each other by 18°. The ridges (9) and the intermediate sections (10) with the through bores (11) are shown in more detail on the right hand side of FIG. 3. In one embodiment, the through bores (11) have a diameter of 1.3 mm. The particular design of the support ring (6) yields an improved interlock of the support ring (6) and the potting material in which the hollow fiber membranes (2) of the capillary dialyzers of the invention are embedded to form the end wall means (3) of the capillary dialyzers of the invention.

In one embodiment of the invention, the inner diameter of the support ring (6) is 34.5±0.1 mm and its outer diameter is 45.6±0.1 mm. In another embodiment of the invention, the inner diameter of the support ring (6) is 38.4±0.1 mm and its outer diameter is 49.3±0.1 mm.

The porous hollow fiber membrane comprises 80-99 wt % of polyethersulfone and 1-20 wt % of polyvinylpyrrolidone (PVP).

An example of a suitable polyethersulfone is a polymer having the general formula —[O-Ph-$SO_2$-Ph-]$_n$-, a weight average molecular weight of about 60,000 to 65,000 Da, preferably 63,000 to 65,000 Da, and a $M_w/M_n$ of about 1.5 to 1.8.

In one embodiment of the invention, the PVP comprised in the porous hollow fiber membrane consists of a high ($\geq$100 kDa) and a low (<100 kDa) molecular weight component and comprises 10-45 wt %, based on the total weight of PVP in the membrane, of a high molecular weight component, and 55-90 wt %, based on the total weight of PVP in the membrane, of a low molecular weight component.

The membrane is asymmetric and has a four-layer structure.

The inner layer of the four-layer structure, i.e. the blood contacting layer and the inner surface of the hollow fiber membrane, is a separation layer in the form of a dense thin layer having, in one embodiment, a thickness of less than 1 μm and a pore size in the nano-scale range. To achieve high selectivity, the pore channels with the responsible pore diameters are short, i.e. below 0.1 μm. The pore channel diameter has a low variation in size.

The next layer in the hollow fiber membrane is the second layer having the form of a sponge structure and, in one embodiment of the present invention, a thickness of about 1 to 15 μm, and serves as a support for the first layer.

The third layer has the form of a finger structure. It provides for mechanical stability on the one hand; on the other hand it has, due to the high void volume, a very low resistance of transport of molecules through the membrane when the voids are filled with water. The third layer has, in one embodiment of the present invention, a thickness of 20 to 60 μm.

The fourth layer is the outer layer, which is characterized by a homogeneous and open pore structure with a defined surface roughness. In one embodiment, the number average size of the pore openings is in the range of 0.5 to 3 μm, further the number of pores on the outer surface is in the range of 20,000 to 100,000 pores per $mm^2$. In one embodiment, this fourth layer has a thickness of about 1 to 10 μm.

The hollow fiber membrane has an inner diameter of from 185 to 195 μm and a wall thickness of from 33 to 37 μm.

The capillary dialyzers of the present invention show sieving coefficients of 1.0 for vitamin B12, 1.0 for inulin, 0.7 for β2-microgobulin, and less than 0.01 for albumin.

The packing density of the hollow fiber membranes in the capillary dialyzers of the present invention is 56%, i.e., the sum of the cross-sectional area of all hollow fiber membranes present in the dialyzer amounts to 56% of the cross-sectional area of the middle section of the dialyzer housing. If n hollow fiber membranes are present in the dialyzer, $D_F$ is the outer diameter of a single hollow fiber membrane, and $D_H$ is the inner diameter of the middle section of the dialyzer housing, the packing density can be calculated according to $n*(D_F/D_H)^2$.

In one embodiment of the capillary dialyzers of the present invention, the dialyzer comprises 12,000 hollow fiber membranes. The nominal surface area of the hollow fiber membranes is 1.8 $m^2$. The dialyzer has an effective membrane surface area of 1.69 $m^2$.

In this embodiment, the tubular section of the housing has an inner diameter of 38 mm at its narrowest point. The support ring has an inner diameter of 38.4 mm. The end cap has an inner diameter of 39.8 mm and an outer diameter of 55.8 mm. The volume of the blood compartment is 93 ml, the residual blood volume is less than 1 ml, and the maximum trans-membrane pressure (TMP) is 600 mmHg.

The dialyzer can be operated at blood flow rates in the range of from 200 to 600 ml/min and dialysate flow rates of from 300 to 800 ml/min. The ultrafiltration coefficient (UFC) of the dialyzer, measured at 37° C. in bovine blood having a hematocrit of 32% and a protein content of 60 g/l, is 54 ml/(h*mmHg).

At $Q_B$=200 ml/min, the blood compartment pressure drop is not more than 100 mmHg. The ultrafiltration rate, measured with bovine blood, is 65 ml/min at TMP=100 mmHg, 86 ml/min at TMP=200 mmHg, and 88 ml/min at TMP=300 mmHg.

At $Q_B$=300 ml/min, the blood compartment pressure drop is not more than 140 mmHg. The ultrafiltration rate, measured with bovine blood, is 112 ml/min at TMP=200 mmHg, 127 ml/min at TMP=300 mmHg, and 130 ml/min at TMP=400 mmHg.

At $Q_B$=400 ml/min, the blood compartment pressure drop is not more than 180 mmHg. The ultrafiltration rate, measured with bovine blood, is 126 ml/min at TMP=200 mmHg, 147 ml/min at TMP=300 mmHg, and 162 ml/min at TMP=400 mmHg.

At $Q_B$=500 ml/min, the blood compartment pressure drop is not more than 220 mmHg. The ultrafiltration rate, measured with bovine blood, is 137 ml/min at TMP=200 mmHg, 158 ml/min at TMP=300 mmHg, and 168 ml/min at TMP=400 mmHg.

At $Q_B$=600 ml/min, the blood compartment pressure drop is not more than 260 mmHg. The ultrafiltration rate, measured with bovine blood, is 144 ml/min at TMP=200 mmHg, 175 ml/min at TMP=300 mmHg, and 187 ml/min at TMP=400 mmHg.

When the dialyzer is operated in hemodialysis mode using a dialysis flow rate of $Q_D$=500 ml/min and an ultrafiltration rate UF of 0 ml/min, the following clearance values are obtained:

| QB [ml/min] | urea | creatinine | phosphate | vitamin B12 |
|---|---|---|---|---|
| 200 | 198 | 195 | 191 | 158 |
| 300 | 281 | 267 | 255 | 191 |
| 400 | 338 | 315 | 297 | 213 |
| 500 | 375 | 348 | 326 | 228 |
| 600 | 401 | 370 | 346 | 240 |

When the dialyzer is operated in hemodialysis mode using a dialysis flow rate of $Q_D$=800 ml/min and an ultrafiltration rate UF of 0 ml/min, the following clearance values are obtained:

| QB [ml/min] | urea | creatinine | phosphate | vitamin B12 |
|---|---|---|---|---|
| 200 | 199 | 198 | 195 | 167 |
| 300 | 292 | 283 | 272 | 208 |
| 400 | 369 | 348 | 330 | 236 |
| 500 | 430 | 398 | 373 | 256 |
| 600 | 477 | 437 | 406 | 272 |

When the dialyzer is operated in hemodiafiltration mode using a dialysis flow rate of $Q_D$=500 ml/min and an ultrafiltration rate UF of 60 ml/min, the following clearance values are obtained:

| QB [ml/min] | urea | creatinine | phosphate | vitamin B12 |
|---|---|---|---|---|
| 200 | 199 | 197 | 194 | 168 |
| 300 | 286 | 274 | 263 | 204 |
| 400 | 348 | 326 | 308 | 226 |
| 500 | 390 | 361 | 339 | 241 |
| 600 | 420 | 387 | 361 | 253 |

When the dialyzer is operated in hemodiafiltration mode using a dialysis flow rate of $Q_D$=800 ml/min and an ultrafiltration rate UF of 60 ml/min, the following clearance values are obtained:

| QB [ml/min] | urea | creatinine | phosphate | vitamin B12 |
|---|---|---|---|---|
| 200 | 200 | 199 | 197 | 175 |
| 300 | 293 | 285 | 276 | 218 |
| 400 | 372 | 352 | 334 | 245 |
| 500 | 434 | 403 | 377 | 265 |
| 600 | 484 | 442 | 411 | 281 |

In another embodiment of the capillary dialyzer, the device comprises 9,600 hollow fiber membranes. The nominal surface area of the hollow fiber membranes is 1.4 m². The device has an effective membrane surface area of 1.35 m².

In this embodiment, the tubular section of the housing has an inner diameter of 34 mm at its narrowest point. The support ring has an inner diameter of 34.5 mm. The end cap has an inner diameter of 36.1 mm and an outer diameter of 52.1 mm. The volume of the blood compartment is 74 ml, the residual blood volume is less than 1 ml, and the maximum trans-membrane pressure (TMP) is 600 mmHg.

The dialyzer can be operated at blood flow rates in the range of from 200 to 500 ml/min and dialysate flow rates of from 300 to 800 ml/min. The ultrafiltration coefficient (UFC) of the dialyzer, measured at 37° C. in bovine blood having a hematocrit of 32% and a protein content of 60 g/l, is 48 ml/(h*mmHg).

At $Q_B$=200 ml/min, the blood compartment pressure drop is not more than 100 mmHg. The ultrafiltration rate, measured with bovine blood, is 63 ml/min at TMP=100 mmHg, 86 ml/min at TMP=200 mmHg, and 96 ml/min at TMP=300 mmHg.

At $Q_B$=300 ml/min, the blood compartment pressure drop is not more than 145 mmHg. The ultrafiltration rate, measured with bovine blood, is 108 ml/min at TMP=200 mmHg, 123 ml/min at TMP=300 mmHg, and 123 ml/min at TMP=400 mmHg.

At $Q_B$=400 ml/min, the blood compartment pressure drop is not more than 190 mmHg. The ultrafiltration rate, measured with bovine blood, is 126 ml/min at TMP=200 mmHg, 144 ml/min at TMP=300 mmHg, and 147 ml/min at TMP=400 mmHg.

At $Q_B$=500 ml/min, the blood compartment pressure drop is not more than 235 mmHg. The ultrafiltration rate, measured with bovine blood, is 139 ml/min at TMP=200 mmHg, 158 ml/min at TMP=300 mmHg, and 165 ml/min at TMP=400 mmHg.

When the dialyzer is operated in hemodialysis mode using a dialysis flow rate of $Q_D$=500 ml/min and an ultrafiltration rate UF of 0 ml/min, the following clearance values are obtained:

| QB [ml/min] | urea | creatinine | phosphate | vitamin B12 |
|---|---|---|---|---|
| 200 | 196 | 191 | 185 | 146 |
| 300 | 272 | 256 | 242 | 174 |
| 400 | 323 | 298 | 278 | 191 |
| 500 | 356 | 326 | 303 | 204 |

When the dialyzer is operated in hemodialysis mode using a dialysis flow rate of $Q_D$=800 ml/min and an ultrafiltration rate UF of 0 ml/min, the following clearance values are obtained:

| QB [ml/min] | urea | creatinine | phosphate | Vitamin B12 |
|---|---|---|---|---|
| 200 | 199 | 195 | 191 | 155 |
| 300 | 286 | 273 | 260 | 189 |
| 400 | 355 | 330 | 309 | 212 |
| 500 | 408 | 373 | 345 | 228 |

When the dialyzer is operated in hemodiafiltration mode using a dialysis flow rate of $Q_D$=500 ml/min and an ultrafiltration rate UF of 60 ml/min, the following clearance values are obtained:

| QB [ml/min] | urea | creatinine | phosphate | vitamin B12 |
|---|---|---|---|---|
| 200 | 198 | 195 | 191 | 161 |
| 300 | 280 | 266 | 253 | 191 |
| 400 | 336 | 312 | 293 | 210 |
| 500 | 374 | 344 | 320 | 222 |

When the dialyzer is operated in hemodiafiltration mode using a dialysis flow rate of $Q_D$=800 ml/min and an ultrafiltration rate UF of 60 ml/min, the following clearance values are obtained:

| QB [ml/min] | urea | creatinine | phosphate | vitamin B12 |
|---|---|---|---|---|
| 200 | 199 | 197 | 195 | 167 |
| 300 | 289 | 278 | 267 | 204 |
| 400 | 361 | 338 | 318 | 227 |
| 500 | 416 | 382 | 355 | 243 |

In still another embodiment of the capillary dialyzer, the device comprises 8,160 hollow fiber membranes. The nominal surface area of the hollow fiber membranes is 1.2 m². The device has an effective membrane surface area of 1.15 m².

In this embodiment, the tubular section of the housing has an inner diameter of 31.5 mm at its narrowest point. The support ring has an inner diameter of 34.5 mm. The end cap has an inner diameter of 36.1 mm and an outer diameter of 52.1 mm. The volume of the blood compartment is 64 ml, the residual blood volume is less than 1 ml, and the maximum trans-membrane pressure (TMP) is 600 mmHg.

The dialyzer can be operated at blood flow rates in the range of from 150 to 400 ml/min and dialysate flow rates of from 300 to 800 ml/min. The ultrafiltration coefficient (UFC) of the dialyzer, measured at 37° C. in bovine blood having a hematocrit of 32% and a protein content of 60 g/l, is 44 ml/(h*mmHg).

At $Q_B$=150 ml/min, the blood compartment pressure drop is not more than 75 mmHg. At $Q_B$=200 ml/min, the blood compartment pressure drop is not more than 100 mmHg. At $Q_B$=300 ml/min, the blood compartment pressure drop is not more than 150 mmHg. At $Q_B$=400 ml/min, the blood compartment pressure drop is not more than 200 mmHg.

When the dialyzer is operated in hemodialysis mode using a dialysis flow rate of $Q_D$=500 ml/min and an ultrafiltration rate UF of 0 ml/min, the following clearance values are obtained:

| QB [ml/min] | urea | creatinine | phosphate | vitamin B12 |
|---|---|---|---|---|
| 150 | 149 | 147 | 144 | 119 |
| 200 | 194 | 188 | 181 | 138 |
| 300 | 265 | 247 | 232 | 163 |
| 400 | 312 | 285 | 265 | 178 |

When the dialyzer is operated in hemodialysis mode using a dialysis flow rate of $Q_D$=800 ml/min and an ultrafiltration rate UF of 0 ml/min, the following clearance values are obtained:

| QB [ml/min] | urea | creatinine | phosphate | vitamin B12 |
|---|---|---|---|---|
| 150 | 150 | 149 | 147 | 126 |
| 200 | 198 | 193 | 188 | 149 |
| 300 | 282 | 266 | 252 | 179 |
| 400 | 346 | 319 | 297 | 198 |

The invention claimed is:

1. A capillary dialyzer comprising:
    a) a housing defining a longitudinally extending internal chamber including a first end and a second end;
    b) a bundle of semi-permeable hollow fiber membranes disposed within the internal chamber and extending longitudinally from the first end of the housing to the second end of the housing, the hollow fiber membranes having an outer surface, and a first end and a second end corresponding to the first end and the second end of the internal chamber;
    c) end wall supports for supporting the first and second ends of the hollow fiber membranes within the internal chamber so as to sealingly separate the first and second ends of the hollow fiber membranes from the outer surface of the hollow fiber membranes between the first and second ends thereof;
    d) a first end cap covering the first end of the housing and a second end cap covering the second end of the housing, the first and second end caps being applied to the first and second ends of the housing in a fluid-tight manner;
    e) an inlet for the introduction of a fluid into the internal chamber and an outlet for the evacuation of a fluid from the internal chamber at a location between the first and second ends of the housing;
    f) support rings disposed between the end wall supports and the housing at the first and second ends of the internal chamber, each support ring includes a number of ridges distributed circumferentially and defining gaps therebetween; and
    g) sealing rings interposed between one of the end wall supports and the first end cap and between another of the end wall supports and the second end cap, respectively;
    wherein a circular groove of the end cap which receives the wall of the housing comprises indentations, which create a fluid conduit between the inside of the capillary dialyzer and its exterior when the end caps are mounted on the housing, and the end caps are fixed to the housing by a weld disposed to close the fluid conduit;
    wherein header sections of the housing comprise notches on the inside surface which extend from the mouth of the housing to the end of a ledge inside the housing on which the support ring is positioned.

2. The capillary dialyzer of claim 1 wherein the end caps have an inner surface which is axially symmetrical with regard to a longitudinal axis of the end cap and an inner surface having the form of a funnel and comprising, in the direction of increasing diameter, a first section taking the form of at least one of a cylinder and a truncated cone, a middle section taking the form of a torus segment and having a radius of 7.0±0.1 mm, and a third section taking the form of a truncated cone, wherein the diameter of the base of the third section is 39.8±0.1 mm and the angle between the base of the third section and the lateral surface of the third section is 9.53±0.05°, and the outer diameter of the end cap is 55.8±0.1 mm.

3. The capillary dialyzer of claim 2, wherein the inner diameter of the middle section of the housing is 38.0±0.1 mm and the inner diameter of the mouth of the housing is 49.6±0.1 mm.

4. The capillary dialyzer of claim 1 wherein the end caps have an inner surface which is axially symmetrical with regard to a longitudinal axis of the end cap and an inner surface having the form of a funnel and comprising, in the direction of increasing diameter, a first section taking the form of at least one of a cylinder and a truncated cone, a middle section taking the form of a torus segment and having a radius of 7.0±0.1 mm, and a third section taking the form of a truncated cone, wherein the diameter of the base of the third section is 36.1±0.1 mm and the angle between the base of the third section and the lateral surface of the third section is 8.85±0.05°, and the outer diameter of the end cap is 52.1±0.1 mm.

5. The capillary dialyzer of claim 4, wherein the inner diameter of the middle section of the housing is 31.5±0.1 mm and the inner diameter of the mouth of the housing is 45.9±0.1 mm.

6. The capillary dialyzer of claim 4, wherein the inner diameter of the middle section of the housing is 34.0±0.1 mm and the inner diameter of the mouth of the housing is 45.9±0.1 mm.

7. The capillary dialyzer of claim 1 wherein each support ring includes a level section defined between adjacent ones of the number of ridges, wherein the level section includes a bore extending therethrough.

8. A capillary dialyzer comprising:
    a) a housing defining a longitudinally extending internal chamber including a first end and a second end;
    b) a bundle of semi-permeable hollow fiber membranes disposed within the internal chamber and extending longitudinally from the first end of the housing to the second end of the housing, the hollow fiber membranes having an outer surface, and a first end and a second end corresponding to the first end and the second end of the internal chamber;
    c) end wall supports for supporting the first and second ends of the hollow fiber membranes within the internal chamber so as to sealingly separate the first and second ends of the hollow fiber membranes from the outer surface of the hollow fiber membranes between the first and second ends thereof;
    d) a first end cap covering the first end of the housing and a second end cap covering the second end of the housing, the first and second end caps being applied to the first and second ends of the housing in a fluid-tight manner;

e) an inlet for the introduction of a fluid into the internal chamber and an outlet for the evacuation of a fluid from the internal chamber at a location between the first and second ends of the housing;

f) support rings disposed between the end wall supports and the housing at the first and second ends of the internal chamber, each support ring includes a number of ridges distributed circumferentially and defining gaps therebetween; and g) sealing rings interposed between one of the end wall supports and the first end cap and between another of the end wall supports and the second end cap, respectively.

9. The capillary dialyzer of claim 8 wherein each support ring includes a level section defined between adjacent ones of the number of ridges, wherein the level section includes a bore extending therethrough.

10. The capillary dialyzer of claim 8 wherein a circular groove of the end cap which receives a wall of the housing comprises indentations, which create a fluid conduit between the inside of the capillary dialyzer and its exterior when the end caps are mounted on the housing, and the end caps are fixed to the housing by a weld disposed to close the fluid conduit.

11. The capillary dialyzer of claim 10 wherein the end caps have an inner surface which is axially symmetrical with regard to a longitudinal axis of the end cap and an inner surface having the form of a funnel and comprising, in the direction of increasing diameter, a first section taking the form of at least one of a cylinder and a truncated cone, a middle section taking the form of a torus segment and having a radius of 7.0±0.1 mm, and a third section taking the form of a truncated cone, wherein the diameter of the base of the third section is 39.8±0.1 mm and the angle between the base of the third section and the lateral surface of the third section is 9.53±0.05°, and the outer diameter of the end cap is 55.8±0.1 mm.

12. The capillary dialyzer of claim 11 wherein the inner diameter of the middle section of the housing is 38.0±0.1 mm and the inner diameter of the mouth of the housing is 49.6±0.1 mm.

13. The capillary dialyzer of claim 10 wherein the end caps have an inner surface which is axially symmetrical with regard to a longitudinal axis of the end cap and an inner surface having the form of a funnel and comprising, in the direction of increasing diameter, a first section taking the form of at least one of a cylinder and a truncated cone, a middle section taking the form of a torus segment and having a radius of 7.0±0.1 mm, and a third section taking the form of a truncated cone, wherein the diameter of the base of the third section is 36.1±0.1 mm and the angle between the base of the third section and the lateral surface of the third section is 8.85±0.05°, and the outer diameter of the end cap is 52.1±0.1 mm.

14. The capillary dialyzer of claim 13 wherein the inner diameter of the middle section of the housing is 31.5±0.1 mm and the inner diameter of the mouth of the housing is 45.9±0.1 mm.

15. The capillary dialyzer of claim 13 wherein the inner diameter of the middle section of the housing is 34.0±0.1 mm and the inner diameter of the mouth of the housing is 45.9±0.1 mm.

16. The capillary dialyzer of claim 8 wherein the end caps have an inner surface which is axially symmetrical with regard to a longitudinal axis of the end cap and an inner surface having the form of a funnel and comprising, in the direction of increasing diameter, a first section taking the form of at least one of a cylinder and a truncated cone, a middle section taking the form of a torus segment and having a radius of 7.0±0.1 mm, and a third section taking the form of a truncated cone, wherein the diameter of the base of the third section is 39.8±0.1 mm and the angle between the base of the third section and the lateral surface of the third section is 9.53±0.05°, and the outer diameter of the end cap is 55.8±0.1 mm.

17. The capillary dialyzer of claim 16, wherein the inner diameter of the middle section of the housing is 38.0±0.1 mm and the inner diameter of the mouth of the housing is 49.6±0.1 mm.

18. The capillary dialyzer of claim 8 wherein the end caps have an inner surface which is axially symmetrical with regard to a longitudinal axis of the end cap and an inner surface having the form of a funnel and comprising, in the direction of increasing diameter, a first section taking the form of at least one of a cylinder and a truncated cone, a middle section taking the form of a torus segment and having a radius of 7.0±0.1 mm, and a third section taking the form of a truncated cone, wherein the diameter of the base of the third section is 36.1±0.1 mm and the angle between the base of the third section and the lateral surface of the third section is 8.85±0.05°, and the outer diameter of the end cap is 52.1±0.1 mm.

19. The capillary dialyzer of claim 18, wherein the inner diameter of the middle section of the housing is 31.5±0.1 mm and the inner diameter of the mouth of the housing is 45.9±0.1 mm.

20. The capillary dialyzer of claim 18, wherein the inner diameter of the middle section of the housing is 34.0±0.1 mm and the inner diameter of the mouth of the housing is 45.9±0.1 mm.

* * * * *